United States Patent
Fukushima et al.

(10) Patent No.: US 10,907,099 B2
(45) Date of Patent: Feb. 2, 2021

(54) COMPOUND, COMPOSITION, CURED OBJECT, OPTICALLY ANISOTROPIC BODY, AND REFLECTIVE FILM

(71) Applicant: FUJIFILM Corporation, Tokyo (JP)

(72) Inventors: Yuki Fukushima, Kanagawa (JP); Ryoji Goto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 55 days.

(21) Appl. No.: 16/424,496

(22) Filed: May 29, 2019

(65) Prior Publication Data

US 2019/0276743 A1    Sep. 12, 2019

Related U.S. Application Data

(63) Continuation of application No. PCT/JP2017/046365, filed on Dec. 25, 2017.

(30) Foreign Application Priority Data

Dec. 27, 2016 (JP) ................................. 2016-253038

(51) Int. Cl.
| | | |
|---|---|---|
| *C09K 19/12* | (2006.01) | |
| *C09K 19/38* | (2006.01) | |
| *C09K 19/56* | (2006.01) | |
| *G02B 5/30* | (2006.01) | |
| *C07C 233/56* | (2006.01) | |
| *G02B 5/08* | (2006.01) | |

(52) U.S. Cl.
CPC ........ *C09K 19/3852* (2013.01); *C07C 233/56* (2013.01); *C09K 19/38* (2013.01); *C09K 19/56* (2013.01); *G02B 5/08* (2013.01); *G02B 5/30* (2013.01); *G02B 5/3016* (2013.01); *C09K 2219/03* (2013.01)

(58) Field of Classification Search
CPC .... C09K 19/38; C09K 19/3852; C09K 19/56; C09K 19/12; C09K 2219/03; C07C 233/56; G02B 5/30; G02B 5/3016
USPC ................................................... 252/299.01
See application file for complete search history.

(56) References Cited

U.S. PATENT DOCUMENTS 6,514,578 B1    2/2003  Farrand
2019/0276743 A1*  9/2019  Fukushima .......... G02B 5/3016

OTHER PUBLICATIONS

"International Search Report (Form PCT/ISA/210) of PCT/JP2017/046365," dated Mar. 13, 2018, with English translation thereof, pp. 1-5.
"Written Opinion of the International Searching Authority (Form PCT/ISA/237) of PCT/JP2017/046365," dated Mar. 13, 2018, with English translation thereof, pp. 1-7.
Karl Maurer, et al., "Carbonyl J Derivatives: A New Class of HIV-1 Integrase Inhibitors," Bioorganic Chemistry, vol. 28, Jun. 2000, pp. 140-155.
Haider Behbehani, et al., "Efficient atom economic approaches towards macrocyclic crown diamides via ring-closing metathesis," Tetrahedron Letters, vol. 43, Jul. 2002, pp. 6421-6426.
"Office Action of Japan Counterpart Application", dated Jun. 9, 2020, with English translation thereof, p. 1-p. 6.

* cited by examiner

*Primary Examiner* — Geraldina Visconti
(74) *Attorney, Agent, or Firm* — JCIPRNET

(57) ABSTRACT

An object of the present invention is to provide a compound (particularly, a liquid crystal compound having excellent light fastness) which has excellent light fastness and can be used for an optically anisotropic body, a reflective film obtained by immobilizing a cholesteric liquid crystalline phase, or the like.
Another object of the present invention is to provide a composition containing the above-mentioned compound (particularly, a liquid crystal compound having excellent light fastness); and a cured object, an optically anisotropic body, and a reflective film, which are obtained by curing the above-mentioned composition.
The compound of the present invention is represented by General Formula (1).

General Formula (1)

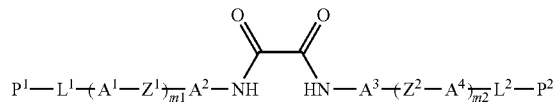

20 Claims, No Drawings

COMPOUND, COMPOSITION, CURED OBJECT, OPTICALLY ANISOTROPIC BODY, AND REFLECTIVE FILM

CROSS-REFERENCE TO RELATED APPLICATIONS

This application is a Continuation of PCT International Application No. PCT/JP2017/046365 filed on Dec. 25, 2017, which claims priority under 35 U.S.C. § 119(a) to Japanese Patent Application No. 2016-253038 filed on Dec. 27, 2016. The above application is hereby expressly incorporated by reference, in its entirety, into the present application.

BACKGROUND OF THE INVENTION

1. Field of the Invention

The present invention relates to a compound, a composition, a cured object, an optically anisotropic body, and a reflective film.

2. Description of the Related Art

A compound (hereinafter also simply referred to as liquid crystal compound) that exhibits liquid crystallinity can be applied to various uses. For example, the liquid crystal compound is applied to production of an optically anisotropic body typified by a retardation film, or to production of a reflective film by immobilizing a cholesteric liquid crystalline phase.

As the liquid crystal compound, for example, the tolan compound having a tolan skeleton (diphenylacetylene skeleton) described in U.S. Pat. No. 6,514,578B is mentioned. In such a tolan compound, an ester group is linked to the tolan skeleton.

SUMMARY OF THE INVENTION

Meanwhile, the above-mentioned optically anisotropic body or the reflective film obtained by immobilizing a cholesteric liquid crystalline phase is further required to have improved light fastness.

In general, as a method for imparting light fastness to an optically anisotropic body, a reflective film obtained by immobilizing a cholesteric liquid crystalline phase, or the like, a method for blending in an adjuvant such as an ultraviolet absorber in addition to a liquid crystal compound at the time of producing the optically anisotropic body, the reflective film, or the like; a method using a liquid crystal compound having excellent light fastness at the time of producing the optically anisotropic body, the reflective film, or the like; and the like are known. Particularly, as in the latter case, in a case where the liquid crystal compound itself has excellent light fastness, the above-mentioned adjuvant is not required to be used. Accordingly, this case is more advantageous in view of production of the optically anisotropic body or the reflective film obtained by immobilizing a cholesteric liquid crystalline phase. Therefore, in recent years, researches on liquid crystal compounds having excellent light fastness have been actively carried out.

The inventors of the present invention carried out examination using a liquid crystal compound of a tolan-skeleton described in U.S. Pat. No. 6,514,578B described above, and elucidated that there is still room for improvement in light fastness of the liquid crystal compound.

An object of the present invention is to provide a compound (particularly, a liquid crystal compound having excellent light fastness) which has excellent light fastness and can be used for an optically anisotropic body, a reflective film obtained by immobilizing a cholesteric liquid crystalline phase, or the like.

Another object of the present invention is to provide a composition containing the above-mentioned compound (particularly, a liquid crystal compound having excellent light fastness); and a cured object, an optically anisotropic body, and a reflective film, which are obtained by curing the above-mentioned composition.

As a result of intensive studies to achieve the above-mentioned objects, the inventors of the present invention have found that the above-mentioned objects can be achieved by a compound represented by General Formula (1), and therefore have completed the present invention.

That is, the inventors have found that the above-described object can be achieved by the following configuration.

[1] A compound represented by General Formula (1).

[2] The compound according to [1], which exhibits liquid crystallinity. [3] The compound according to [1] or [2], in which an aspect ratio of molecule is 4 or more.

[4] The compound according to any one of [1] to [3], in which a molecular structure is asymmetric.

[5] The compound according to any one of [1] to [4], in which at least one of $A^2$ or $A^3$ is a divalent aromatic hydrocarbon ring group having a substituent, or a divalent aromatic heterocyclic group having a substituent.

[6] The compound according to [5], in which the substituent is a fluorine atom, a chlorine atom, a fluoroalkyl group, an alkoxy group, or an alkyl group.

[7] The compound according to [5] or [6], in which the substituent is a fluoroalkyl group, an alkoxy group, or an alkyl group.

[8] The compound according to any one of [1] to [7], in which $A^1$ to $A^4$ are divalent benzene ring groups.

[9] The compound according to any one of [1] to [8], in which $Z^1$ and $Z^2$ are each independently a single bond, —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —N=CH—, —CH=CH—CO—NH—, —NH—CO—CH=CH—, —CH=CH—CO—S—, —S—CO—CH=CH—, or —C≡C—.

[10] The compound according to any one of [1] to [9], in which $Z^1$ and $Z^2$ are each independently a single bond, —COO—, —OCO—, —CO—NH—, —NH—CO—, or —C≡C—.

[11] The compound according to any one of [1] to [10], in which $L^1$ is a group represented by General Formula (2), and $L^2$ is a group represented by General Formula (3).

[12] The compound according to [11], in which $X^1$ and $X^2$ are each independently a single bond, —O—, —COO—, or —OCO—.

[13] The compound according to [11] or [12], in which n1 and n2 are each 1.

[14] A composition comprising the compound according to any one of [1] to [13].

[15] The composition according to [14], further comprising a polymerization initiator.

[16] The composition according to [14] or [15], further comprising a chiral agent.

[17] A cured object, which is obtained by curing the composition according to any one of [14] to [16].

[18] An optically anisotropic body, which is obtained by curing the composition according to any one of [14] to [16].

[19] A reflective film, which is obtained by curing the composition according to any one of [14] to [16].

According to the present invention, it is possible to provide a compound having excellent light fastness (particularly, a liquid crystal compound having excellent light fastness).

In addition, according to the present invention, it is possible to provide a composition containing the above-mentioned compound (particularly, a liquid crystal compound having excellent light fastness); and a cured object, an optically anisotropic body, and a reflective film, which are obtained by curing the above-mentioned composition.

DESCRIPTION OF THE PREFERRED EMBODIMENTS

Hereinafter, the present invention will be described in detail.

The explanation of the configuration requirements described below is based on representative embodiments of the present invention; however, the present invention is not intended to be limited to such embodiments.

According to the present specification, a numerical value range indicated using "to" means a range including the numerical values described before and after "to" as a lower limit value and an upper limit value.

In addition, in the present specification, a "(meth)acryloyloxy group" is a description representing both an acryloyloxy group and a methacryloyloxy group.

<Compound represented by General Formula (1)>

A compound represented by General Formula (1) according to the embodiment of the present invention exhibits excellent light fastness, because the compound has an -$A^2$-NH—CO—CO—NH-$A^3$- group at a predetermined position ($A^2$ and $A^3$ each independently represent a divalent aromatic hydrocarbon ring group or divalent aromatic heterocyclic group, which may have a substituent).

In addition, the compound represented by General Formula (1) according to the embodiment of the present invention is has a structure in which, in each of the aromatic hydrocarbon rings or the aromatic heterocyclic rings in $A^1$, $A^2$, $A^3$, and $A^4$, two bonding sites of each of $A^1$, $A^2$, $A^3$, and $A^4$ are not located on carbon atoms adjacent to each other. That is, for example, in a case where each of $A^1$, $A^2$, $A^3$, and $A^4$ is a divalent benzene ring group, the two bonding sites of each of $A^1$, $A^2$, $A^3$, and $A^4$ are arranged in a position other than the ortho position. In other words, the two bonding sites of each of $A^1$, $A^2$, $A^3$, and $A^4$ are arranged in the meta position or para position. The compound represented by General Formula (1) according to the embodiment of the present invention has a relatively large aspect ratio of molecule due to this structure, and thus exhibits liquid crystallinity.

For a compound to show liquid crystallinity, it is intended that the compound has a property of expressing a mesophase between a crystalline phase (low temperature side) and an isotropic phase (high temperature side) in a case where a temperature is changed. As a specific observation method, optical anisotropy and fluidity derived from a liquid crystalline phase can be confirmed by making an observation under a polarizing microscope while heating or lowering a temperature of a compound with a hot stage system FP90, manufactured by Mettler-Toledo International Inc., or the like.

Hereinafter, the compound represented by General Formula (1) will be described in detail.

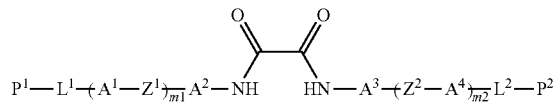

General Formula (1)

In General Formula (1), $P^1$ and $P^2$ each independently represent a hydrogen atom or a substituent, and at least one of $P^1$ or $P^2$ represents a polymerizable group. Among these, from the viewpoint of superior reactivity, both $P^1$ and $P^2$ are preferably polymerizable groups.

A type of the substituent is not particularly limited, and a known substituent is mentioned. As the substituent, for example, a halogen atom, an alkyl group, an alkoxy group, an aryl group, a nitrile group, an isothiocyanate group, a hydroxyl group, an amino group, a carboxyl group, a sulfonamide group, an N-sulfonylamide group, an acyl group, an acyloxy group, and an alkoxycarbonyl group are mentioned. Each of the above groups may be further substituted with a substituent. For example, a hydrogen atom in the alkyl group may be substituted with a fluorine atom. As the substituent, a polymerizable group is preferable.

A type of the polymerizable group is not particularly limited, and a known polymerizable group is mentioned. From the viewpoint of reactivity, a functional group that can be subjected to addition polymerization reaction is preferable, and a polymerizable ethylenically unsaturated group or a cyclic polymerizable group is more preferable. As the polymerizable group, for example, a (meth)acryloyloxy group, a vinyl group, a maleimide group, an acetyl group, a styryl group, an allyl group, an epoxy group, an oxetane group, and a group containing these groups are mentioned. A hydrogen atom in each of the above groups may be substituted with another substituent such as a halogen atom.

As preferable specific examples of the polymerizable group, groups represented by General Formulae (P-1) to (P-19) are mentioned. In the following formulae, * represents a bonding position.

(P-1)

(P-2)

(P-3)

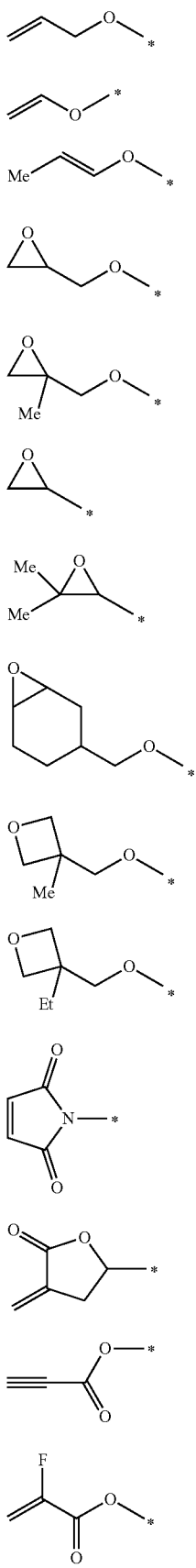

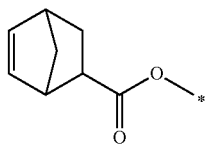

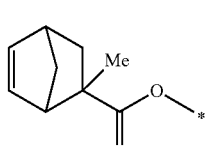

$L^1$ and $L^2$ each independently represent a single bond or a divalent linking group.

The divalent linking group is not particularly limited, and examples thereof include a divalent hydrocarbon group (which may be a divalent saturated hydrocarbon group or a divalent aromatic hydrocarbon ring group. The divalent saturated hydrocarbon group which may be linear, branched, or cyclic preferably has 1 to 20 carbon atoms, and examples thereof include an alkylene group. In addition, the divalent aromatic hydrocarbon ring group preferably has 5 to 20 carbon atoms, and examples thereof include a phenylene group. Besides that, the divalent hydrocarbon group may be an alkenylene group or an alkynylene group.), a divalent heterocyclic group, —O—, —S—, —SO$_2$—, —NR$^1$—, —CO—(—C(=O)—), —COO—(—C(—C(=O)O—), —OCO—, —NR$^1$—CO—, —CO—NR$^1$—, —SO$_3$—, —SO$_2$NR$^1$—, —NR$^1$—SO$_2$—, —CH=N—, —N=CH—, and a group obtained by combining two or more thereof. Here, R$^1$ represents a hydrogen atom or an alkyl group (preferably having 1 to 10 carbon atoms).

A hydrogen atom in the divalent linking group may be substituted with another substituent such as a halogen atom.

Among these, from the viewpoint of further improving liquid crystallinity of the compound represented by General Formula (1), it is preferable that $L^1$ is a group represented by General Formula (2), and $L^2$ is a group represented by General Formula (3).

$$*1\text{-}(S^1\text{-}X^1)_{n1}\text{-}*2 \qquad \text{General Formula (2)}$$

$$*3\text{-}(X^2\text{-}S^2)_{n2}\text{-}*4 \qquad \text{General Formula (3)}$$

In General Formulae (2) and (3), $S^1$ and $S^2$ each independently represent an alkylene group which may contain a heteroatom.

The number of carbon atoms contained in the alkylene group is not particularly limited, and is preferably 1 to 30, more preferably 1 to 20, and even more preferably 1 to 10.

In a case where a heteroatom is contained in the alkylene group, a type of the heteroatom is not particularly limited. Examples thereof include an oxygen atom, a nitrogen atom, a sulfur atom, a selenium atom, and a tellurium atom. Among these, the heteroatom is preferably contained in the alkylene group, in a form of —Y$^1$—, —N(R$^2$)—, —C(=Y$^2$)—, —CON(R$^3$)—, —C(=Y$^3$)Y$^4$—, —SO$_t$—, —SO$_2$N(R$^4$)—, or a group obtained by combining these.

$Y^1$ to $Y^4$ each independently represent an oxygen atom, a sulfur atom, a selenium atom, or a tellurium atom. t represents an integer of 1 to 3. $R^2$, $R^3$, and $R^4$ each independently represent a hydrogen atom or an alkyl group.

Among these, $S^1$ and $S^2$ are preferably alkylene groups having 1 to 20 carbon atoms of which one —CH$_2$— or two or more adjacent —$CH_2$—'s each independently may be substituted with —O—, —COO—, —OCO—, or —OCO—O—.

$X^1$ and $X^2$ each independently represent a single bond, —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CH=N—N=CH—, —CF=CF—, or —C≡C—.

Among these, it is preferable that $X^1$ and $X^2$ are each independently a single bond, —O—, —COO—, or —OCO—.

n1 and n2 each independently represent an integer of 0 to 8. Among them, n1 and n2 each independently is preferably 0 to 4, and is more preferably 1. It is even more preferable that both n1 and n2 be 1.

In General Formula (2), *1 represents a bonding position with $P^1$ in General Formula (1), and *2 represents a bonding position with $A^1$ in General Formula (1). In General Formula (3), *3 represents a bonding position with $A^4$ in General Formula (1), and *4 represents a bonding position with $P^2$ in General Formula (1).

$A^1$ to $A^4$ each independently represent a divalent aromatic hydrocarbon ring group or divalent aromatic heterocyclic group, which may have a substituent.

Among these, from the viewpoint of further improving solubility of the compound represented by General Formula (1), a divalent aromatic hydrocarbon ring group having a substituent or a divalent aromatic heterocyclic group having a substituent is preferable. In particular, it is more preferable that at least one of $A^2$ or $A^3$ be a divalent aromatic hydrocarbon ring group having a substituent, or a divalent aromatic heterocyclic group having a substituent.

In a case of introducing a substituent to $A^2$ or $A^3$, in the aromatic hydrocarbon rings or the aromatic heterocyclic rings in $A^2$ or $A^3$, the above-mentioned substituent is preferably introduced to a carbon atom adjacent to an atom which is a bonding position with —NH—CO—CO—NH—. By introducing a substituent to the above-mentioned position, —NH—CO—CO—NH— and the substituent interact with each other, and the compound represented by General Formula (1) exhibits excellent solubility and liquid crystallinity.

The aromatic hydrocarbon ring group may be a monocyclic structure or a polycyclic structure. As specific examples of a ring constituting the aromatic hydrocarbon ring group, for example, a benzene ring, a biphenyl ring, a naphthalene ring, an anthracene ring, a phenanthrene ring, and a fluorene ring are mentioned. Among these, a benzene ring is preferable.

The aromatic heterocyclic group may be a monocyclic structure or a polycyclic structure. As specific examples of a ring constituting the aromatic heterocyclic group, a furan ring, a thiophene ring, a pyrrole ring, an oxazole ring, an isoxazole ring, an oxadiazole ring, a thiazole ring, an isothiazole ring, a thiadiazole ring, an imidazole ring, a pyrazole ring, a triazole ring, a furazan ring, a tetrazole ring, a pyridine ring, a pyridazine ring, a pyrimidine ring, a pyrazine ring, a triazine ring, a tetrazine ring, and a benzothiazole ring are mentioned.

The aromatic hydrocarbon ring group and the aromatic heterocyclic group may have a substituent. A type of the substituent is not particularly limited, and a known substituent is mentioned. For example, a halogen atom, an alkyl group, an alkoxy group, an aryl group, a hydroxyl group, an amino group, a carboxyl group, a sulfonamide group, an N-sulfonylamide group, an acyl group, an acyloxy group, a cyano group, a nitro group, and an alkoxycarbonyl group are mentioned. Each of the above groups may be further substituted with a substituent. For example, a hydrogen atom in the alkyl group may be substituted with a fluorine atom. In addition, the number of the substituent is not particularly limited, and the aromatic hydrocarbon ring group and the aromatic heterocyclic group may have one substituent or may have a plurality of substituents.

Among these, from the viewpoint of further improving solubility of the compound represented by General Formula (1), the substituent is preferably a fluorine atom, a chlorine atom, a fluoroalkyl group, an alkoxy group, or an alkyl group, and more preferably a fluoroalkyl group, an alkoxy group, or an alkyl group.

The number of carbon atoms in the fluoroalkyl group and alkyl group, and the number of carbon atoms of the alkyl group in the alkoxy group are not particularly limited, and are preferably 1 to 10, more preferably 1 to 5, and even more preferably 1 to 3, with 1 being particularly preferable.

The fluoroalkyl group is a group in which at least one hydrogen atom in the alkyl group is substituted with a fluorine atom, and is preferably a group in which all hydrogen atoms in the alkyl group are substituted with fluorine atoms (so-called perfluoroalkyl group is preferable).

In each of the aromatic hydrocarbon rings or the aromatic heterocyclic rings in $A^1$, $A^2$, $A^3$, and $A^4$, two bonding sites of each of $A^1$, $A^2$, $A^3$, and $A^4$ are not located on carbon atoms adjacent to each other. That is, for example, in a case where each of $A^1$, $A^2$, $A^3$, and $A^4$ is a benzene ring group, the two bonding sites of each of $A^1$, $A^2$, $A^3$, and $A^4$ are located on a carbon atom other than carbon atoms at the ortho position on the benzene ring. In other words, the two bonding sites of each of $A^1$, $A^2$, $A^3$, and $A^4$ are located on a carbon atom at the meta position or para position on the benzene ring. Specifically, in the compound represented by General Formula (1), for example, in a case where $A^1$ is a benzene ring group and m1 is 1, a carbon atom at the meta position or para position on the benzene ring is bonded to $L^1$ and $Z^1$.

An aspect ratio of the compound represented by General Formula (1) is preferably 4 or more. In a case where the aspect ratio is 4.4 or more, excellent liquid crystallinity tends to be exhibited. Accordingly, for example, in a case where each of $A^1$ to $A^4$ is a benzene ring group, the two bonding sites of each of $A^1$, $A^2$, $A^3$, and $A^4$ are preferably located at the para position from the viewpoint of increasing an aspect ratio of molecule. That is, it is preferable that $A^1$ to $A^4$ be benzene ring groups bonded at the 1-position and the 4-position.

An upper limit of the aspect ratio is not particularly limited, but is 7 or less in many cases.

An aspect ratio of molecule can be calculated based on the most stable structure of the molecule, which is calculated by density-functional calculation performed using a computer.

$Z^1$ and $Z^2$ each independently represent a single bond or a divalent linking group.

Definition and exemplification of the divalent linking group are the same as the definition and exemplification of the divalent linking group represented by $L^1$ and $L^2$ as described above.

Among them, from the viewpoint of exhibiting superior effects of the present invention, $Z^1$ and $Z^2$ are each independently preferably a single bond, —O—, —S—, —OCH₂—, —CH₂O—, —CH₂CH₂—, —CO—, —COO—, —OCO—, —CO—S—, —S—CO—, —O—CO—O—, —CO—NH—, —NH—CO—, —SCH₂—, —CH₂S—, —CF₂O—, —OCF₂—, —CF₂S—, —SCF₂—, —CH=CH—COO—, —CH=CH—OCO—, —COO—CH=CH—, —OCO—CH=CH—, —COO—CH₂CH₂—, —OCO—CH₂CH₂—, —CH₂CH₂—COO—, —CH₂CH₂—OCO—, —COO—CH₂—, —OCO—CH₂—, —CH₂—COO—, —CH₂—OCO—, —CH=CH—, —N=N—, —CH=N—N=CH—, —CF=CF—, —CH=N—, —N=CH—, —CH=CH—CO—NH—, —NH—CO—CH=CH—, —CH=CH—CO—S—, —S—CO—CH=CH—, or —C≡C—, and are more preferably a single bond, —COO—, —OCO—, —CO—NH—, —NH—CO—, or —C≡C—.

m1 and m2 each independently represent an integer of 1 to 3. Among these, from the viewpoint of exhibiting superior effects of the present invention, m1 and m2 are preferably 1. In addition, in a case where m1 and m2 are 2 or greater, a plurality of A¹'s, A⁴'s, Z¹'s, and Z²'s may be the same as or different from each other.

From the viewpoint of further improving the solubility, the compound represented by General Formula (1) prefer-ably has an asymmetric molecular structure. A method for rendering a molecular structure asymmetric is not particularly limited. Examples thereof include a method for imparting different substituents to A² and A³, and the like.

Refractive index anisotropy Δn of the compound represented by General Formula (1) is not particularly limited. The Δn is preferably 0.2 or more, and more preferably 0.25 or more. An upper limit thereof is not particularly limited, and is 0.60 or less in many cases.

As a method of measuring the Δn, a method using a wedge-shaped liquid crystal cell described on page 202 of the Liquid Crystal Handbook (edited by Liquid Crystal Handbook Editing Committee, published by Maruzen Co., Ltd.) is generally used. In a case of a compound which is liable to crystallize, it is also possible to carry out evaluation with a mixture thereof with other liquid crystals and to estimate Δn from extrapolated values thereof.

The Δn corresponds to a measured value at a wavelength of 550 nm at 30° C.

The compound represented by General Formula (1) can be synthesized by a known method.

As the compound represented by General Formula (1), for example, the following are exemplified.

a-1
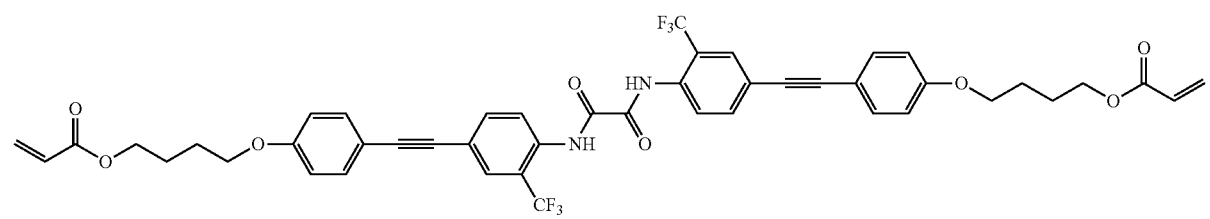

a-2
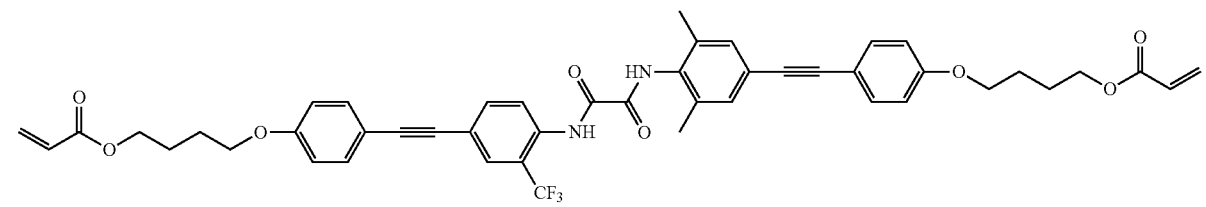

a-3
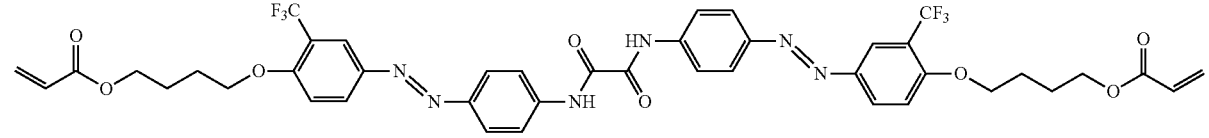

a-4
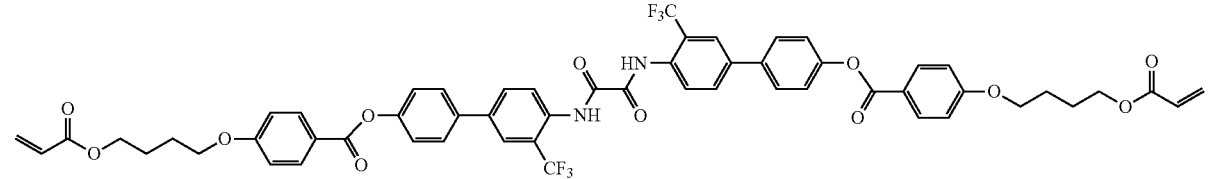

a-5
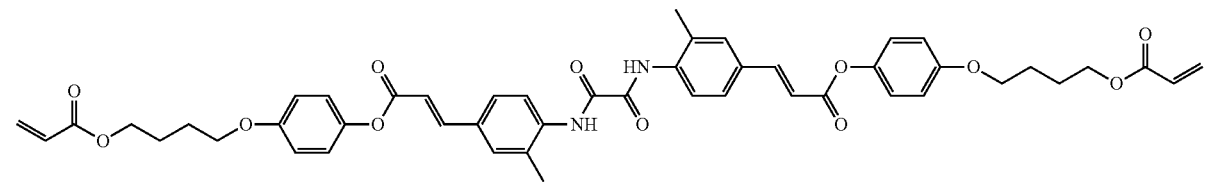

-continued
a-6
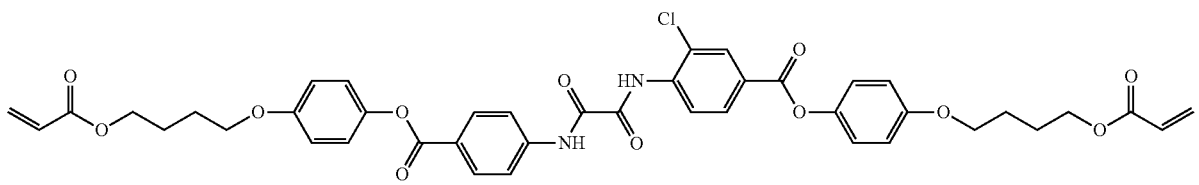
a-7
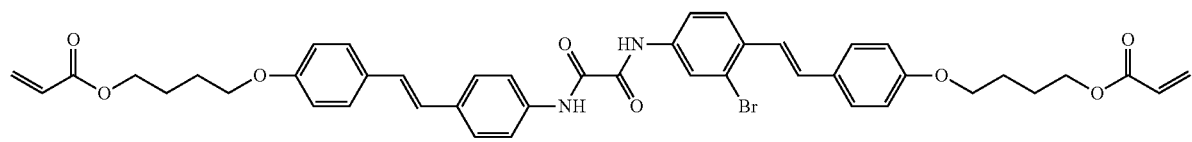
a-8
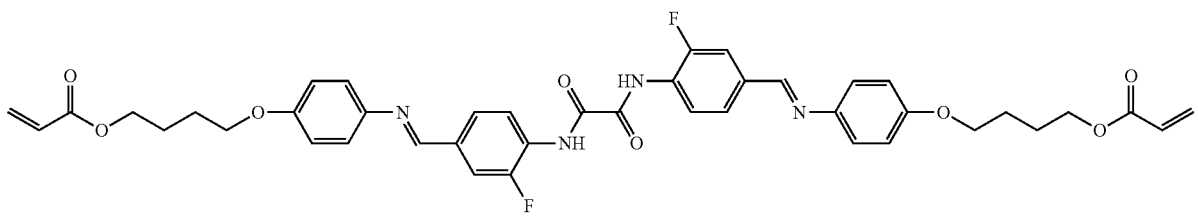
a-9
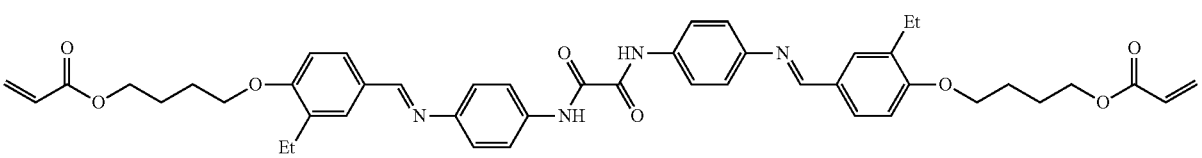
a-10
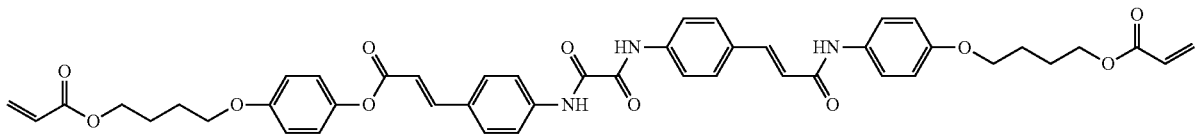
a-11
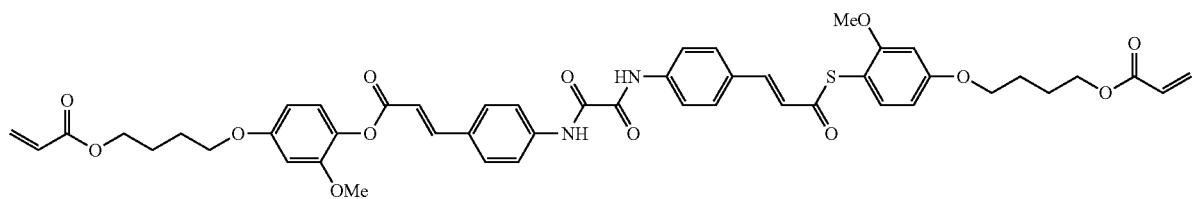
a-12
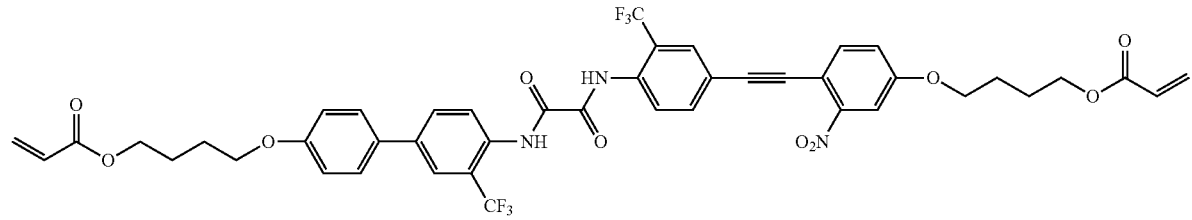
a-13
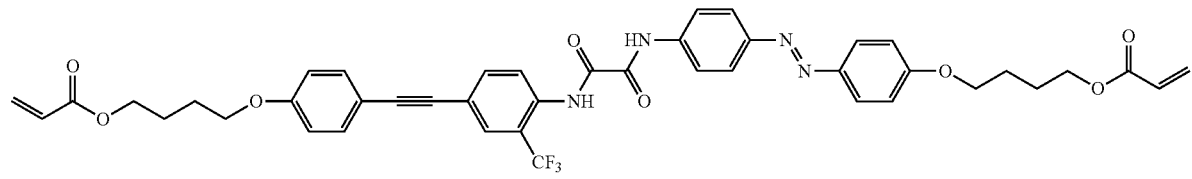

-continued
a-14
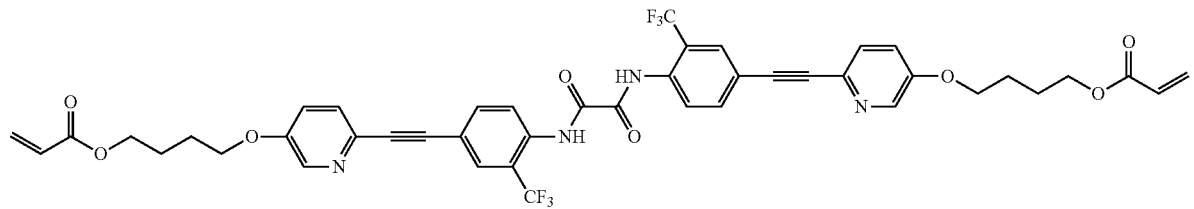
a-15
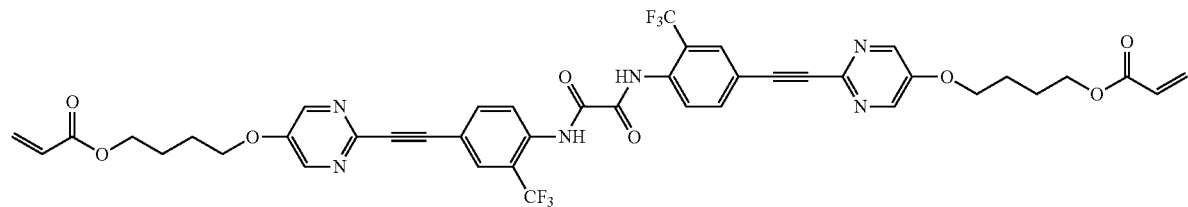
a-16
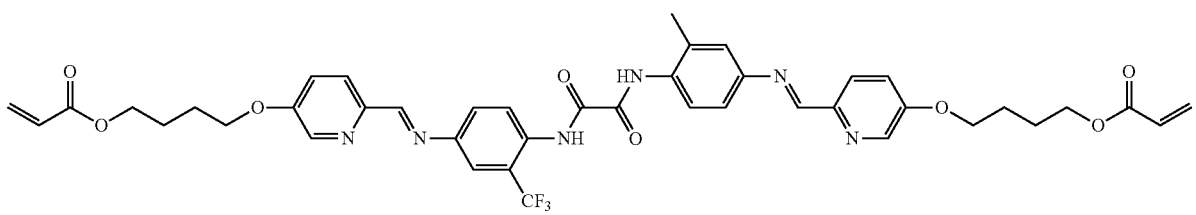
a-17
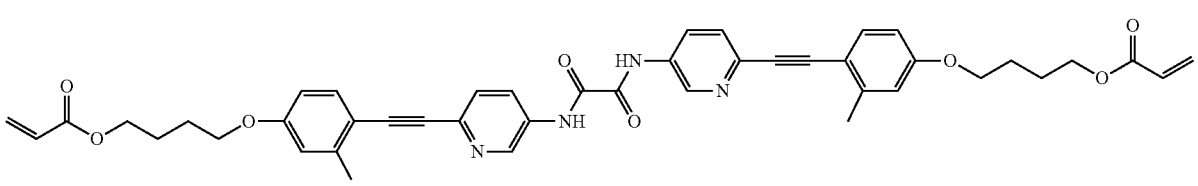
a-18
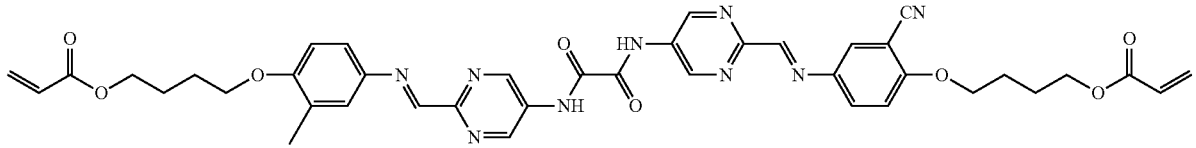
a-19
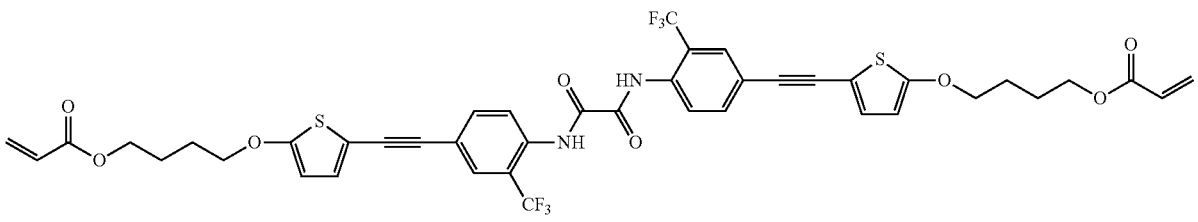
a-20
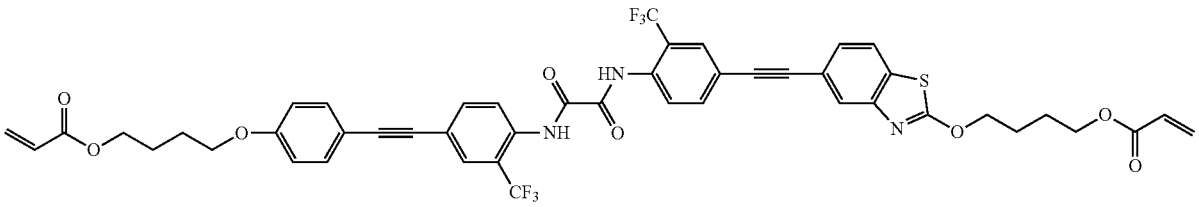

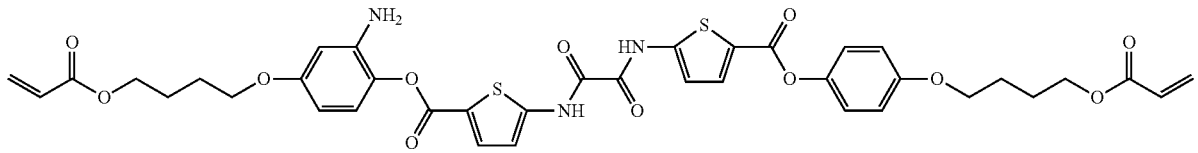

a-21

<Composition, Cured Object, Optically Anisotropic Body, and Reflective Film>

The compound represented by General Formula (1) can be used in the form of a composition containing this compound. Components other than the compound represented by General Formula (1) may be contained in the composition.

Hereinafter, other components contained in the composition will be described in detail.

(Polymerization Initiator)

The composition may contain a polymerization initiator.

The polymerization initiator is preferably a photopolymerization initiator which is capable of initiating a polymerization reaction by ultraviolet irradiation. As the photopolymerization initiator, for example, an α-carbonyl compound, acyloin ether, an α-hydrocarbon-substituted aromatic acyloin compound, a polynuclear quinone compound, a phenazine compound, and an oxadiazole compound are mentioned.

A content of the polymerization initiator in the composition is not particularly limited, and is preferably 0.1% to 20% by mass, and more preferably 1% to 8% by mass, with respect to the entire mass of the compound represented by General Formula (1).

(Chiral Agent)

The composition may contain a chiral agent. In a case where the composition contains the chiral agent, a cholesteric liquid crystalline phase can be formed.

A type of the chiral agent is not particularly limited. The chiral agent may be liquid crystalline or non-liquid crystalline. The chiral agent generally contains an asymmetric carbon atom. However, an axial asymmetric compound or a planar asymmetric compound which does not contain any asymmetric carbon atom can also be used as the chiral agent. As the axial asymmetric compound or the planar asymmetric compound, binaphthyl, helicene, paracyclophane, and derivatives thereof are mentioned. The chiral agent may have a polymerizable group.

Besides the above, the composition may also contain other additives such as a solvent, an alignment control agent, an antioxidant, an ultraviolet absorber, a sensitizer, a stabilizer, a plasticizer, a chain transfer agent, a polymerization inhibitor, an anti-foaming agent, a leveling agent, a thickener, a flame retardant, a surfactant, a dispersant, and a coloring material such as a dye and a pigment.

In addition, the compound represented by General Formula (1) according to the embodiment of the present invention and another liquid crystal compound may be used in combination.

(Curing Method and Cured Object)

A method of curing (polymerizing and curing) the above composition is not particularly limited, and a known method can be adopted. For example, a form having a step X in which a predetermined substrate and the composition are brought into contact with each other to form a composition layer on the substrate, and a step Y in which the composition layer is subjected to a heat treatment so that the compound represented by General Formula (1) is aligned, and then is subjected to a curing treatment. According to the present form, the compound represented by General Formula (1) can be immobilized in an aligned state, and a layer in which a so-called optically anisotropic body or a cholesteric liquid crystalline phase is immobilized can be formed.

Hereinafter, procedures for the step X and the step Y will be described in detail.

The step X is a step of bringing a predetermined substrate into contact with the composition to form a composition layer on the substrate. A type of the substrate to be used is not particularly limited, and known substrates (for example, a resin substrate, a glass substrate, a ceramic substrate, a semiconductor substrate, and a metal substrate) are mentioned.

A method of bringing the substrate into contact with the composition is not particularly limited, and examples thereof include a method of coating the composition on the substrate and a method of immersing the substrate in the composition.

After bringing the substrate into contact with the composition, if necessary, a drying treatment may be carried out in order to remove a solvent from the composition layer on the substrate.

The step Y is a step of subjecting the composition layer to a heat treatment so that the compound represented by General Formula (1) is aligned, and then subjecting the same to a curing treatment.

By subjecting the composition layer to a heat treatment, the compound represented by General Formula (1) is aligned and a liquid crystalline phase is formed. For example, in a case where a chiral agent is contained in the composition layer, a cholesteric liquid crystalline phase is formed.

A condition for the heat treatment is not particularly limited, and an optimal condition is selected depending on a type of the compound represented by General Formula (1).

A method for the curing treatment is not particularly limited, and a photo-curing treatment and a thermal-curing treatment are mentioned. Among these, a light irradiation treatment is preferable, and an ultraviolet irradiation treatment is more preferable.

For the ultraviolet irradiation, a light source such as an ultraviolet lamp is used.

The cured object obtained by the above treatment corresponds to a layer in which a liquid crystalline phase is immobilized. In particular, in a case where the composition contains a chiral agent, a layer is formed in which a cholesteric liquid crystalline phase is immobilized.

These layers do not need to exhibit liquid crystallinity anymore. More specifically, for example, as a state in which the cholesteric liquid crystalline phase is "immobilized," the most typical and preferable form is a state in which alignment of the compound represented by General Formula (1) which is a cholesteric liquid crystalline phase is retained. More specifically, the state is preferably a state in which within a temperature range of usually 0° C. to 50° C., and, under more severe conditions, −30° C. to 70° C., no fluidity is exhibited in the layer, no changes in alignment form occur due to an external field or an external force, and an immobilized alignment form can be kept in a stable and continuous manner.

A cured object is obtained by subjecting the composition to a curing treatment as described above.

The cured object obtained by curing the composition according to the embodiment of the present invention can be applied to various uses, and, for example, an optically anisotropic body and a reflective film are mentioned. In other words, an optically anisotropic body or a reflective film obtained by curing the above composition is mentioned as a suitable form.

The optically anisotropic body is intended to have a substance having optical anisotropy.

In addition, the reflective film corresponds to a layer in which the above-described cholesteric liquid crystalline phase is immobilized, and can reflect light in a predetermined reflection band.

EXAMPLES

[Preparation of Compounds and Evaluation Thereof]

Hereinafter, the present invention will be described more specifically with reference to examples. Materials, reagents, proportions, operations, and the like shown in the following examples can be appropriately changed without departing from the gist of the present invention. Accordingly, the scope of the present invention is not limited to the following specific examples.

Synthesis Example 1: Synthesis of Compound a-1

Compound a-1 was synthesized according to the following scheme.

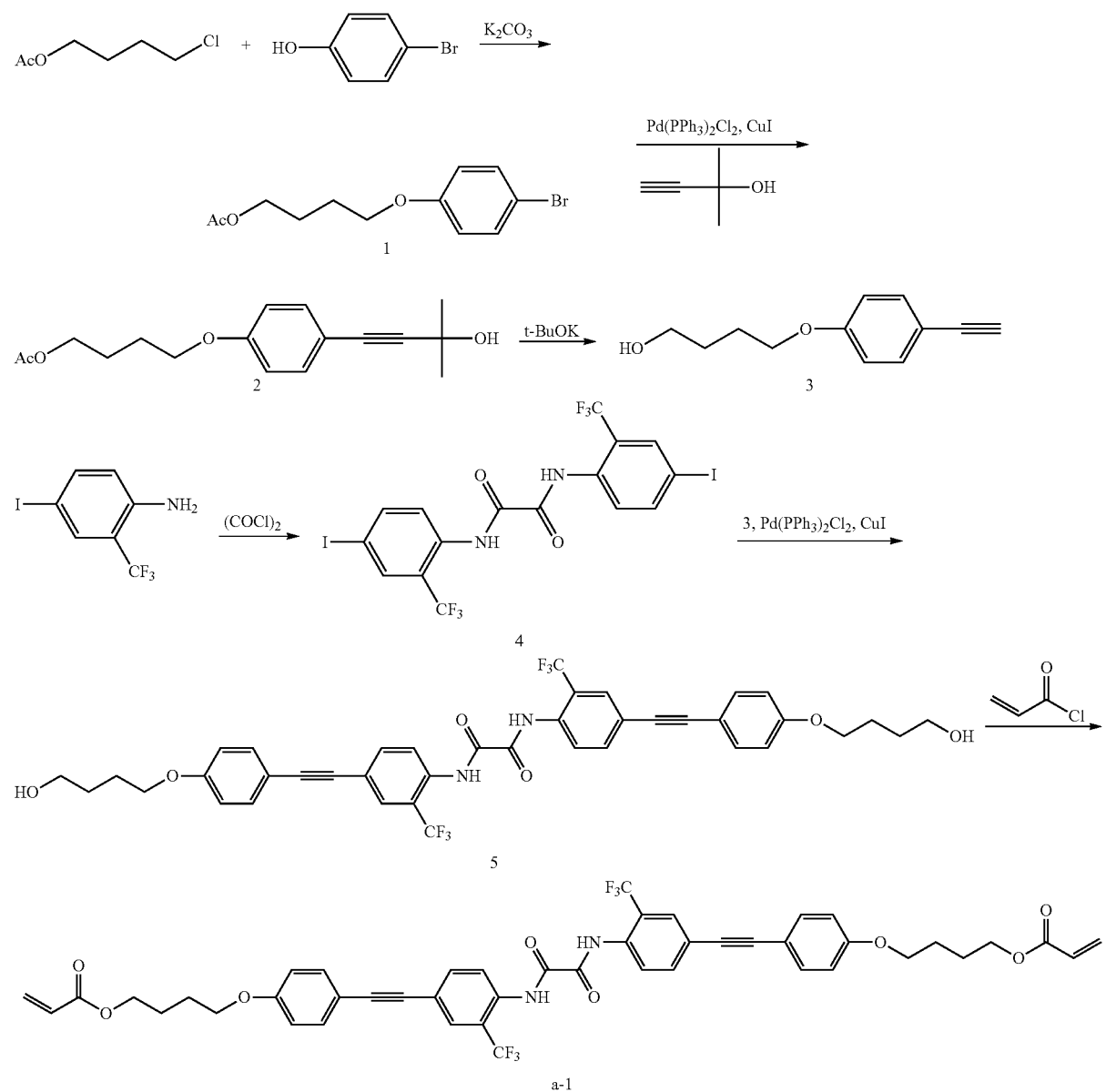

(1) Synthesis of Compound 1

Under a nitrogen atmosphere, 4-bromophenol (170 g, 0.983 mol) was dissolved in dimethyl acetamide (690 ml). Potassium carbonate (163 g, 1.18 mol) and potassium iodide (19.6 g, 0.118 mol) were added to the resulting solution, and a temperature of the solution was elevated to 70° C. Thereafter, 4-chlorobutyl acetate (148 g, 0.983 mol) was added dropwise to the solution, and the solution was stirred at 90° C. for 5 hours. After cooling the solution to room temperature, insoluble matters were removed from the solution by filtration, the insoluble matters thus separated were washed with toluene, and the toluene used for washing and the filtrate previously obtained were mixed. The resulting solution was washed twice with 1 N hydrochloric acid, twice with saline, once with 1 N sodium hydroxide aqueous solution, twice with pure water, and once with saline, respectively. Magnesium sulfate was added to the washed solution. The resulting solution was filtered and the filtrate was collected. Then, the solvent was distilled off from the filtrate under reduced pressure. The resulting residue was purified by flash column chromatography to obtain Compound 1 (249 g) in the form of colorless oil.

(2) Synthesis of Compound 2

Under a nitrogen atmosphere, Compound 1 (240 g, 0.836 mol) and 3-methyl-1-butyn-3-ol (105 g, 1.25 mol) were dissolved in triethylamine (720 ml). After nitrogen bubbling of the resulting solution for 30 minutes, $Pd(PPh_3)_2Cl_2$ (3.52 g, 5.01 mmol) and CuI (1.59 g, 8.35 mmol) were added to the solution, and the resulting solution was stirred under heating reflux for 4 hours. Thereafter, $Pd(PPh_3)_2Cl_2$ (1.76 g, 2.51 mmol) and CuI (0.80 g, 4.2 mmol) were further added to the solution and the resulting solution was stirred under heating reflux for 2 hours. After cooling the solution to room temperature, insoluble matters were removed from the solution by filtration, the insoluble matters thus separated were washed with ethyl acetate, and the ethyl acetate used for washing and the filtrate previously obtained were mixed. The resulting solution was washed twice with pure water and once with saline, respectively, and magnesium sulfate was added to the washed solution. The resulting solution was filtered and the filtrate was collected. Then, the solvent was distilled off from the filtrate under reduced pressure. The resulting residue was purified by flash column chromatography to obtain Compound 2 (215 g) in the form of a brown oil.

(3) Synthesis of Compound 3

Under a nitrogen atmosphere, Compound 2 (210 g, 0.723 mol) was dissolved in isopropyl alcohol (1,300 ml). Potassium tert-butoxide (284 g, 2.53 mol) was added to the resulting solution and the solution was stirred at 105° C. for 4 hours. After cooling the solution to room temperature, 1 N hydrochloric acid was added to the solution, followed by extraction with ethyl acetate. The organic layer obtained by the extraction was washed twice with pure water and once with saline, respectively, and magnesium sulfate was added to the washed organic layer. The obtained organic layer was filtered to collect the filtrate, and then the solvent was distilled off from the filtrate under reduced pressure. The resulting residue was purified by flash column chromatography to obtain Compound 3 (107 g) as a brown solid.

(4) Synthesis of Compound 4

4-Iodo-2-trifluoromethylaniline (10.01 g, 34.88 mmol) was dissolved in N-methylpyrrolidone (30 ml). Oxalyl chloride (2.21 ml, 25.8 mmol) was added dropwise to the resulting solution under ice cooling, and the solution was stirred at room temperature for 8 hours. Next, ethyl acetate and 1 N hydrochloric acid were added to the solution, and then the mixture was extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was dissolved in ethyl acetate, hexane was added to the resulting solution, and a reprecipitation treatment was carried out to obtain Compound 4 (5.18 g) as a brown solid.

(5) Synthesis of Compound 5

Under a nitrogen atmosphere, Compound 3 (2.33 g, 12.2 mmol) and Compound 4 (3.50 g, 5.57 mmol) were dissolved in a mixed solution of dimethylformamide (30 ml) and triethylamine (4 ml). After nitrogen bubbling of the resulting solution for 30 minutes, $Pd(PPh_3)_2Cl_2$ (193 mg, 0.275 mmol) and CuI (107 mg, 0.563 mmol) were added to the solution, and the solution was stirred at 55° C. for 3.5 hours. After cooling the solution to room temperature, insoluble matters were removed from the solution by filtration, the insoluble matters thus separated were washed with ethyl acetate, and the ethyl acetate used for washing and the filtrate previously obtained were mixed. The resulting solution was washed once with a saturated aqueous solution of ammonium chloride, once with pure water, and once with saline, respectively. Sodium sulfate was added to the washed solution. The resulting solution was filtered and the filtrate was collected. Then, the solvent was distilled off from the filtrate under reduced pressure. The resulting residue was purified by flash column chromatography to obtain Compound 5 (4.19 g) as a brown solid.

(6) Synthesis of Compound a-1

Compound 5 (4.20 g, 5.58 mmol) was dissolved in dimethylacetamide (85 ml). Acryl chloride (1.09 ml, 13.5 mmol) was added to the resulting solution under ice cooling, and the solution was stirred at room temperature for 3 hours. Furthermore, acryl chloride (1.09 ml, 13.5 mmol) was added to the resulting solution under ice cooling, and the solution was stirred at room temperature for 3 hours. Next, 1 N hydrochloric acid was added to the solution, and then the mixture was extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography. The resulting residue was dissolved in chloroform, methanol was added to the resulting solution, and a reprecipitation treatment was carried out to obtain Compound a-1 (1.98 g) as a white solid.

$^1$H-NMR (CDCl$_3$): δ=1.89 (m, 8H), 4.01 (t, 4H), 4.25 (t, 4H), 5.82 (dt, 2H), 6.11 (dd, 2H), 6.39 (dt, 2H), 6.88 (d, 4H), 7.47 (d, 4H), 7.74 (d, 2H), 7.81 (s, 2H), 8.49 (d, 2H), 9.93 (d, 2H)

Synthesis Example 2: Synthesis of Compound a-2

Compound a-2 was synthesized according to the following scheme.

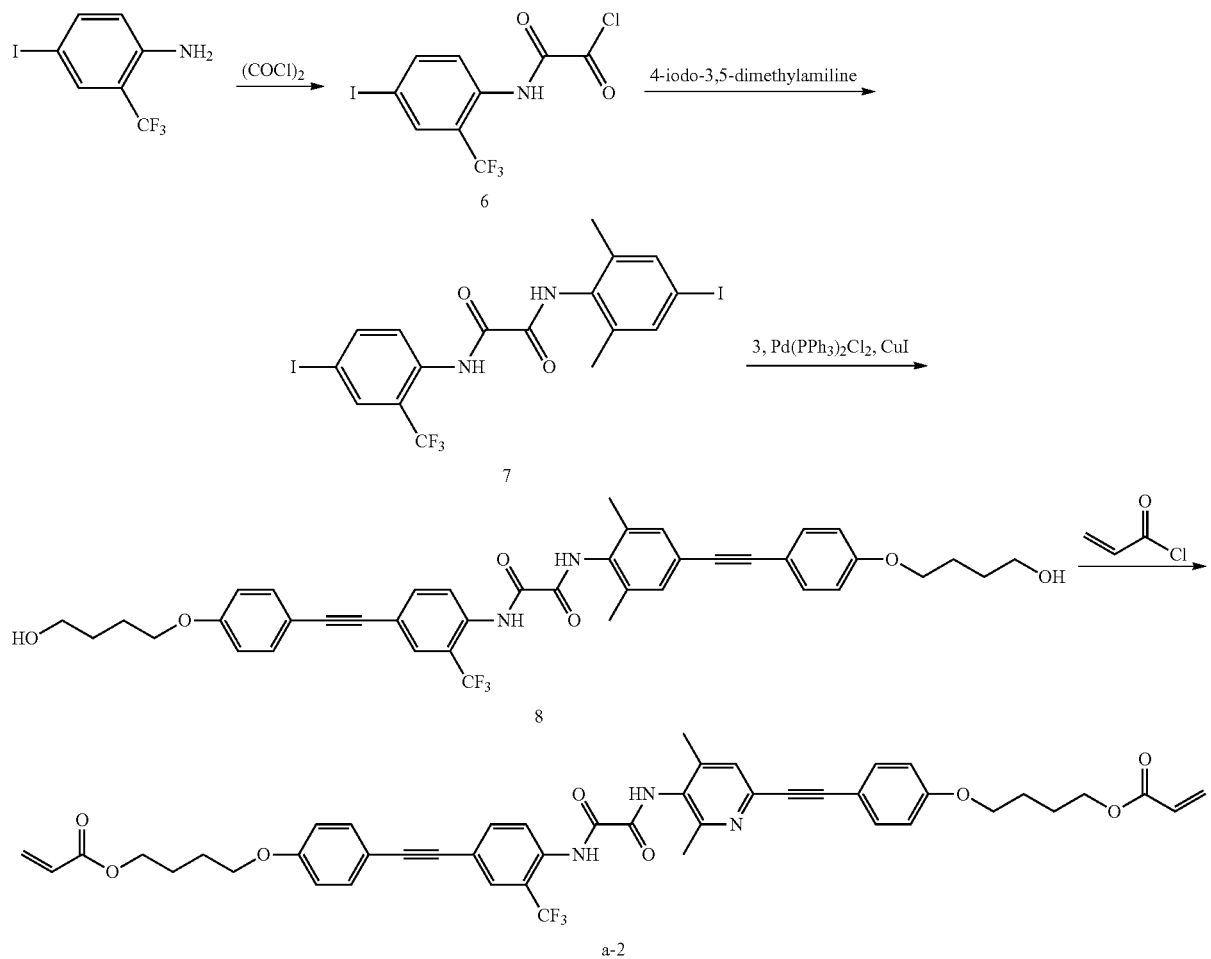

(1) Synthesis of Compound 6

Oxalyl chloride (6.30 ml, 73.5 mmol) was dissolved in 1,2-dichloroethane (20 ml). At −10° C., a solution of 4-iodo-2-trifluoromethylaniline (7.01 g, 24.4 mmol) in 1,2-dichloroethane (10 ml) was added dropwise to the resulting solution, and the solution was stirred for 4 hours under ice cooling. Next, ethyl acetate and 1 N hydrochloric acid were added to the solution, and then the mixture was extracted with ethyl acetate. The organic layer obtained by extraction was washed once with saline, and sodium sulfate was added to the washed organic layer. Thereafter, the solvent was distilled off from the solution under reduced pressure. Therefore, Compound 6 (9.21 g) as a white solid was obtained.

(2) Synthesis of Compound 7

Compound 6 (9.21 g, 24.4 mmol) was dissolved in tetrahydrofuran (5 ml). Under ice cooling, a solution of 4-iodo-3,5-dimethylaniline (6.02 g, 24.4 mmol) in N-methylpyrrolidone (20 ml) was added dropwise to the resulting solution, and the solution was stirred at room temperature for 3 hours. Next, ethyl acetate and hexane was added to the resulting solution, and a crystallization treatment was carried out to obtain Compound 7 (7.39 g) as a green solid.

(3) Synthesis of Compound 8

Under a nitrogen atmosphere, Compound 3 (3.61 g, 19.0 mmol) and Compound 7 (5.00 g, 8.50 mmol) were dissolved in a mixed solution of dimethylformamide (30 ml) and triethylamine (12 ml). After nitrogen bubbling of the resulting solution for 1 hour, Pd(PPh$_3$)$_2$Cl$_2$ (298 mg, 0.425 mmol) and CuI (161 mg, 0.850 mmol) were added to the solution, and the solution was stirred at 55° C. for 2 hours. After cooling the solution to room temperature, ethyl acetate and 1 N hydrochloric acid were added to the solution, followed by extraction with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography to obtain Compound 8 (5.81 g) as a brown solid.

(4) Synthesis of Compound a-2

Compound 8 (6.06 g, 8.50 mmol) was dissolved in dimethylacetamide (30 ml). Acryl chloride (1.65 ml, 20.4 mmol) was added to the resulting solution under ice cooling, and the solution was stirred at room temperature for 2 hours. Furthermore, acryl chloride (0.82 ml, 10.1 mmol) was added to the resulting solution under ice cooling, and the solution was stirred at room temperature for 2 hours. Next, 1 N hydrochloric acid was added to the solution, and then the mixture was extracted with ethyl acetate. The organic layer obtained by extraction was washed once with saline, and sodium sulfate was added to the washed organic layer. The obtained organic layer was filtered to collect the filtrate, and then the solvent was distilled off from the filtrate under reduced pressure. The resulting residue was purified by flash column chromatography. The resulting residue was dissolved in chloroform, methanol was added to the resulting solution, and a reprecipitation treatment was carried out to obtain Compound a-2 (2.62 g) as a white solid.

$^1$H-NMR (CDCl$_3$): δ=1.90 (m, 8H), 2.28 (s, 6H), 4.02 (m, 4H), 4.26 (m, 4H), 5.82 (d, 2H), 6.11 (dd, 2H), 6.40 (d, 2H), 6.88 (m, 4H), 7.29 (s, 2H), 7.46 (m, 4H), 7.74 (d, 1H), 7.81 (s, 1H), 8.49 (d, 1H), 8.79 (s, 1H), 9.90 (s, 1H)

<Synthesis of Comparative Compound b-1>

As described in U.S. Pat. No. 6,514,578B, Compound b-1 to be described later was synthesized.

(Solubility Measurement)

Ethyl methyl ketone was added dropwise to each of the compounds, and a concentration (% by mass) of the compound in the obtained ethyl methyl ketone solution in a case where the compound was completely dissolved in the solution was measured as "solubility". It is intended that a higher numerical value of solubility indicates excellent solubility in ethyl methyl ketone. The results are shown in Table 1.

(Calculation of Aspect Ratio)

The most stable structure of each compound was calculated by density-functional calculation performed using a computer, and therefore an aspect ratio thereof was calculated. Specifically, as a program used for optimization of the molecular structure, Gaussian 03 Rev. D. 02 (trade name, manufactured by Gaussain Inc.) was used, B3LYP/6-31G (d) was used as a basis function, and default values were used for convergence conditions.

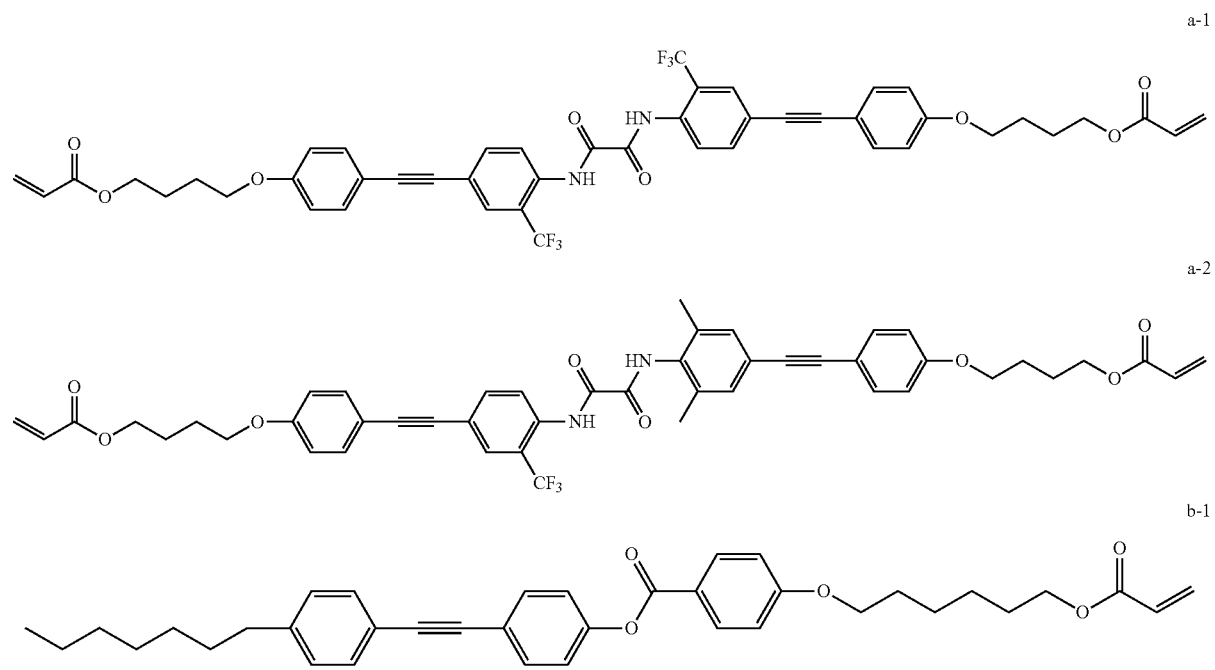

<Various Evaluations>

Using above-mentioned Compounds a-1 and a-2, and Comparative Compound b-1, the following various evaluations were carried out.

(Phase Transition Temperature Measurement)

Each of the compounds was heated on a hot stage and observed under a polarizing microscope to investigate phase transition behavior. The results are shown in Table 1. In the table, "Cr," "Ne," and "Iso" represent a crystalline state, a nematic phase, and an isotropic liquid, respectively.

In Table 1, in the phase transition temperature column, numerical values in parenthesis represent crystallization temperatures during temperature lowering.

In addition, for example, "Cr 176 (128) Ne 200 Iso" of Compound a-1 represents that a phase transition temperature from a crystalline state to a nematic phase is 176° C., and a phase transition temperature from a nematic phase to an isotropic liquid is 200° C.

As shown in Table 1, it was confirmed that all compounds according to the embodiment of the present invention exhibited a liquid crystalline phase.

(Measurement of Light Fastness)

Each (5 mg) of the compounds was dissolved in acetonitrile (20 ml), sealed in a 1 cm quartz cell, and the quartz cell was irradiated with ultraviolet light under a condition of 3 J/cm$^2$ using EXECURE 3000-W manufactured by HOYA-SCHOTT CORPORATION, so that a residual rate of each compound was measured. Amounts (masses) of each compound before and after light irradiation were calculated using liquid chromatography. The results are shown in Table 1. In the table, "A" represents a residual rate of equal to or greater than 80%, "B" represents a residual rate of equal to or greater than 50% and less than 80%, and "C" represents a residual rate of less than 50%.

TABLE 1

| Evaluated compound | Phase transition | Solubility (MEK) | Aspect ratio | Evaluation of light fastness |
|---|---|---|---|---|
| Compound (a-1) of present invention | Cr 176 (128) Ne 200 Iso | 2% | 5.20 | A |

TABLE 1-continued

| Evaluated compound | Phase transition | Solubility (MEK) | Aspect ratio | Evaluation of light fastness |
|---|---|---|---|---|
| Compound (a-2) of present invention | Cr 119 Ne 196 Iso | 14% | 4.47 | A |
| Comparative Compound (b-1) | Cr 80 Ne 158 Iso | | 5.15 | C |

Based on the results in Table 1, it became clear that Compounds (a-1 and a-2) of the present invention are excellent in light fastness. Meanwhile, it became clear that the compound of the comparative example (Comparative Compound b-1) does not satisfy the desired requirement for light fastness.

In addition, it was confirmed that Compounds (a-1 and a-2) of the present invention and the compound of the comparative example (Comparative Compound b-1) have an aspect ratio of 4 or more, and thus exhibit liquid crystallinity.

Furthermore, from the comparison between Compound (a-1) of the present invention and Compound (a-2) of the present invention, it became clear that solubility becomes superior in a case where the molecular structure is asymmetric (Compound (a-2) of the present invention).

[Preparation of Composition and Evaluation Thereof]
<Preparation of Composition (Coating Liquid) 1>

Compound a-1 of the present invention, a fluorine-based horizontal alignment agent shown below, a polymerization initiator, and a solvent were mixed to prepare Coating Liquid 1 having the following composition.

| | |
|---|---|
| Compound a-1 of the present invention | 100 parts by mass |
| Fluorine-based horizontal alignment agent | 0.1 parts by mass |
| Polymerization initiator (IRGACURE 819 (manufactured by Ciba Japan)) | 4 parts by mass |
| Solvent (chloroform) | Amount such that a solute concentration becomes 5% by mass |

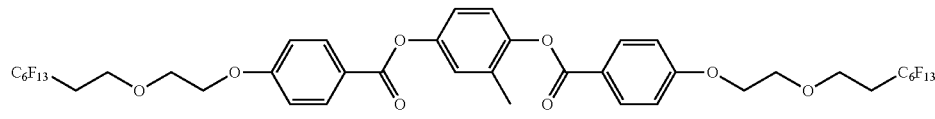

Fluorine-based horizontal alignment agent

<Preparation of Composition (Coating Liquid 2)>

Compound a-2 of the present invention, the above-mentioned fluorine-based horizontal alignment agent, a polymerization initiator, and a solvent were mixed to prepare Coating Liquid 2 having the following composition.

| | |
|---|---|
| Compound a-2 of the present invention | 100 parts by mass |
| Fluorine-based horizontal alignment agent | 0.1 parts by mass |
| Polymerization initiator (IRGACURE 819 (manufactured by Ciba Japan)) | 4 parts by mass |
| Solvent (chloroform) | Amount such that a solute concentration becomes 5% by mass |

<Formation of Optically Anisotropic Body 1>

A surface of an alignment film in a glass substrate attached with an alignment film (SE-130 manufactured by Nissan Chemical Industries, Ltd.) was subjected to a rubbing treatment. Next, Coating Liquid 1 was coated on the alignment film at room temperature with a spin coater so that a thickness of the dried film became 0.7 μm. The coated film was heated in an atmosphere at 155° C. for 1 minute to horizontally align Compound a-1 of the present invention. Next, the coated film was irradiated with ultraviolet light (UV) (23.4 mW/cm$^2$ for 12.8 seconds) at 150° C. in a nitrogen atmosphere using HOYA-SCHOTT EXECURE-3000W manufactured by HOYA CANDEO OPTRONICS, and Compound a-1 of the present invention was immobilized. Therefore, Optically Anisotropic Body 1 was produced on a glass substrate. The retardation of the produced Optically Anisotropic Body 1 was measured with AxoScan manufactured by Axometrix, and a value thereof was 158.2 nm.

<Formation of Optically Anisotropic Body 2>

A surface of an alignment film in a glass substrate attached with an alignment film (SE-130 manufactured by Nissan Chemical Industries, Ltd.) was subjected to a rubbing treatment. Next, Coating Liquid 2 was coated on the alignment film at room temperature with a spin coater so that a thickness of the dried film became 0.7 μm. The coated film was heated in an atmosphere at 70° C. for 1 minute to horizontally align Compound a-2 of the present invention. Next, the coated film was irradiated with ultraviolet light (UV) (23.4 mW/cm$^2$ for 12.8 seconds) at 60° C. in a nitrogen atmosphere using HOYA-SCHOTT EXECURE-3000W manufactured by HOYA CANDEO OPTRONICS, and Compound a-2 of the present invention was immobilized. Therefore, Optically Anisotropic Body 2 was produced on a glass substrate. The retardation of the produced Optically Anisotropic Body 2 was measured with AxoScan manufactured by Axometrix, and a value thereof was 175.3 nm.

What is claimed is:

1. A compound represented by General Formula (1),

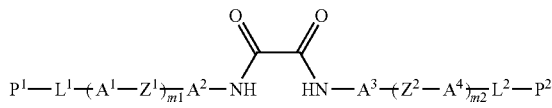

General Formula (1)

in General Formula (1), $P^1$ and $P^2$ each independently represent a hydrogen atom or a polymerizable group, and at least one of $P^1$ or $P^2$ represents the polymerizable group; $L^1$ and $L^2$ each independently represent a single bond or a divalent linking group; $A^1$ to $A^4$ each independently represent a divalent aromatic hydrocarbon ring group or divalent aromatic heterocyclic group, which may have a substituent; where, in each of the aromatic hydrocarbon rings or the aromatic heterocyclic rings in $A^1$, $A^2$, $A^3$, and $A^4$, two bonding sites of each of $A^1$, $A^2$, $A^3$, and $A^4$ are not located on carbon atoms adjacent to each other, and the two bonding sites of each of $A^1$, $A^2$, $A^3$, and $A^4$ are for bonding each of $A^1$, $A^2$, $A^3$, and $A^4$ with adjacent groups; $Z^1$ and $Z^2$ each independently represent a single bond or a divalent linking group; and m1 and m2 each independently represent an integer of 1 to 3, and in a case where m1 and m2 are 2 or greater, a plurality of $A^1$'s, $A^4$'s, $Z^1$'s, and $Z^2$'s may be the same as or different from each other.

2. The compound according to claim 1, which exhibits liquid crystallinity.

3. The compound according to claim 1, wherein an aspect ratio of molecule of General Formula (1) is 4 or more.

4. The compound according to claim 1, wherein a molecular structure of General Formula (1) is asymmetric.

5. The compound according to claim 1, wherein at least one of $A^2$ or $A^3$ is a divalent aromatic hydrocarbon ring group having a substituent, or a divalent aromatic heterocyclic group having a substituent.

6. The compound according to claim 5, wherein the substituent is a fluorine atom, a chlorine atom, a fluoroalkyl group, an alkoxy group, or an alkyl group.

7. The compound according to claim 5, wherein the substituent is a fluoroalkyl group, an alkoxy group, or an alkyl group.

8. The compound according to claim 1, wherein $A^1$ to $A^4$ are divalent benzene ring groups.

9. The compound according to claim 1, wherein $Z^1$ and $Z^2$ are each independently a single bond, —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —CH=N—, —N=CH—, —CH=CH—CO—NH—, —NH—CO—CH=CH—, —CH=CH—CO—S—, —S—CO—CH=CH—, or —C≡C—.

10. The compound according to claim 1, wherein $Z^1$ and $Z^2$ are each independently a single bond, —COO—, —OCO—, —CO—NH—, —NH—CO—, or —C≡C—.

11. The compound according to claim 1, wherein $L^1$ is a group represented by General Formula (2), and $L^2$ is a group represented by General Formula (3),

*1—(S$^1$—X$^1$)$_{n1}$—*2          General Formula (2)

*3—(X$^2$—S$^2$)$_{n2}$—*4          General Formula (3)

in General Formulae (2) and (3), $S^1$ and $S^2$ each independently represent an alkylene group which may contain a heteroatom; $X^1$ and $X^2$ each independently represent a single bond, —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—; and n1 and n2 each independently represent an integer of 0 to 8, and in General Formula (2), *1 represents a bonding position with $P^1$ in General Formula (1), and *2 represents a bonding position with $A^1$ in General Formula (1); and in General Formula (3), *3 represents a bonding position with $A^4$ in General Formula (1), and *4 represents a bonding position with $P^2$ in General Formula (1).

12. The compound according to claim 11, wherein $X^1$ and $X^2$ are each independently a single bond, —O—, —COO—, or —OCO—.

13. The compound according to claim 11, wherein n1 and n2 are each 1.

14. A composition comprising the compound according to claim 1.

15. The composition according to claim 14, further comprising a polymerization initiator.

16. The composition according to claim 14, further comprising a chiral agent.

17. A cured object, which is obtained by curing the composition according to claim 14.

18. An optically anisotropic body, which is obtained by curing the composition according to claim 14.

19. A reflective film, which is obtained by curing the composition according to claim 14.

20. The compound according to claim 2, wherein an aspect ratio of molecule of General Formula (1) is 4 or more.

* * * * *